United States Patent [19]

Frey

[11] 3,980,739

[45] Sept. 14, 1976

[54] METHOD OF PURIFYING TRIARYL PHOSPHITES

[75] Inventor: Jean-Marie Frey, Pontoise, France

[73] Assignee: Rhone-Poulenc Industries, Paris, France

[22] Filed: Jan. 27, 1975

[21] Appl. No.: 544,394

[30] Foreign Application Priority Data

Jan. 25, 1974 France .............................. 74.02497

[52] U.S. Cl. .............................. 260/989; 260/990
[51] Int. Cl.$^2$ .......................................... C07F 9/145
[58] Field of Search .............................. 260/989, 990

[56] References Cited
UNITED STATES PATENTS

| | | | |
|---|---|---|---|
| 3,275,717 | 9/1966 | Butler | 260/989 X |
| 3,553,298 | 1/1971 | Hodan et al. | 260/989 X |
| 3,787,537 | 1/1974 | DeMarcq | 260/989 X |
| 3,852,288 | 12/1974 | Baum et al. | 260/989 X |

*Primary Examiner*—Richard L. Raymond
*Attorney, Agent, or Firm*—McDougall, Hersh & Scott

[57] ABSTRACT

The subject matter of the invention is a method of preparing pure triaryl phosphites by treatment with a hydrogen compound of nitrogen. The invention can be applied to decolorizing triaryl phosphites with a view to using them as stabilizers, antioxidants and complex-forming agents in the plastics and rubber industries.

10 Claims, No Drawings

METHOD OF PURIFYING TRIARYL PHOSPHITES

The invention relates to a method of purifying triaryl phosphites.

Triaryl phosphites are currently prepared in industry by reacting phosphorus trichloride with a phenol, slightly in excess of the stoichiometric quantity, by the well known reaction:

$$PCl_3 + 3 Ar\,OH \rightarrow (ArO)_3P + 3\,HCl$$

wherein Ar represents an aryl radical which is either unsubstituted or substituted more often by a hydrocarbon chain. The excess phenol and the hydrochloric acid formed are separated by distillation under vacuum, to yield a triaryl phosphite which is still fairly impure. The crude triaryl phosphite is generally a colored substance (200 to 500 on the HAZEN scale) with an acid value still between 0.3 and 0.7, for it is very difficult, if not impossible, to elimiate all the residual hydrochloric acid.

Triaryl phosphites are known to be useful in many fields, particularly in the plastics and rubber industries, as stabilizers, antioxidants and complex-forming agents inter alia. As the demand for triaryl phosphites has progressively increased, it has been found necessary to use purified substances, that is to say, substances freed from any odor, color and traces of residual acidity, since these impurities have been found to affect the quality of the final products in which the triaryl phosphite is incorporated.

It has previously been proposed to neutralize the hydrochloric acid, as the reaction for the formation of the triaryl phosphite progresses, with neutralizing agents such as alkaline carbonates, trimethylamine, triethylamine, pyridine, aniline and N-N-diethylaniline. However, this process cannot be used industrially since it involves using a large quantity of neutralizing agents and the crude final product still retains a fairly definite color.

It has also been proposed to distill triaryl phosphite. However, apart from the fact that it requires special apparatus, the conventional method has the disadvantage of consuming a large amount of energy and of being extremely slow. In addition, some triaryl phosphites have little heat stability and there is a great risk of loss by decomposition.

The object of the invention is thus to avoid these disadvantages and, in particular, to improve the physicochemical properties of triaryl phosphites and to obtain a virtually colorless, odorless product with considerable, if not total, reduction in its residual acidity, without requiring special installation or any appreciable amount of handling.

Applicant has unexpectedly discovered that the addition of very small quantities of at least one hydrogen compound of nitrogen, of a basic character, to triaryl phosphites produces a considerable improvement in decolorizing and deodorizing and at the same time virtually complete neutralization of the residual acidity.

According to the invention, crude triaryl phosphite containing traces of hydrochloric acid is subjected to treatment with a hydrogen compound of nitrogen, of a basic character, at from 20° to 120°C.

Triaryl phosphites which can undergo the treatment of the invention include triphenylphosphites and trialkylphenylphosphites obtained from substituted phenols, such as tricresylphosphites and triethylphenylphosphites. In cases where the trialkylphenylphosphites are solid or viscous at the temperature at which the purifying treatment is to take place, the treatment may advantageously be carried out in the presence of an appropriate solvent.

The hydrogen compounds of nitrogen are the monoazotized ($HNH_2$) and diazotized ($NH_2-NH_2$) derivatives. Ammonia $HNH_2$ is used preferably in gas form; hydrazine $NH_2\text{-}NH_2$ is preferably used in hydrate form.

The proportions of the hydrogen compound of nitrogen vary from an effective minimum of about 0.005% to about 0.5% by weight, based on the weight of phosphite. As far as the gaseous ammonia is concerned, it is preferable to use quantities of up to 2 to 10 times the quantity required for neutralization.

The temperature of the reaction for the elimination of hydrochloric acid, which takes place simultaneously with the decolorizing reaction, is preferably from 80° to 100°C.

In one embodiment of the invention, the hydrogen compound of nitrogen is added in the presence of an inert gas, such as nitrogen or argon.

A completely unexpected finding is that, of the basic compounds which will neutralize the residual acidity of the triaryl phosphites, only hydrogen compounds of nitrogen have a definite decolorizing reaction on the said phosphites, unlike other neutralizing agents. The specific nature of this action has been brought out in comparative tests. Primary, secondary and tertiary organic amines as well as alkaline and alkaline-earth salts of inorganic acids have proved to be ineffective as decolorizing agents.

The examples which follow are given purely to illustrate the invention and cannot therefore be considered as restricting its scope.

EXAMPLE 1

By reacting phosphorus trichloride with phenol and then distilling off any excess phenol present under vacuum, a triphenyl phosphite is obtained with an acid value of 0.4, HAZEN coloring of 350 and a pungent smell. 0.035% by weight of hydrazine hydrate relative to the weight of the phosphite is then added in one operation, at 80°C. The mixture is vigorously agitated.

A few minutes later the hydrazine hydrochloride which has precipitated is filtered at about 50°C. The triphenyl phosphite then has the following properties:

AV — 0
Coloring — 30 HAZEN
Odor — negligible

EXAMPLE 2

A crude triphenyl phosphite with an acid value of 0.6, HAZEN coloring of 300 and a pungent smell is treated under the same conditions as in Example 1, with 0.035% by weight of hydrazine hydrate. When the hydrochloride precipitate has been filtered, the triphenyl phosphite has the following properties:

AV — 0.2
Coloring — 50 HAZEN
Odor — weak

EXAMPLE 3

A triphenyl phosphite with an acid value of 0.2, HAZEN coloring of 350 and a pungent smell is treated under the same conditions as in Example 1, using 0.02% by weight of hydrazine hydrate. When the hydrazine hydrochloride precipitate has been filtered, the triphenyl phosphite has the following properties:

AV — 0.1
Coloring — 50 HAZEN
Odor — negligible

EXAMPLE 4

Starting with the same crude reaction product as in Example 1, a quantity of ammonia gas corresponding to five times the quantity required to neutralize the residual acidity is passed through at 80°C. When the ammonium chloride precipitate has been filtered, the triphenyl phosphite has the following properties:

AV — 0.2
Coloring — 60 HAZEN
Odor — negligible

EXAMPLE 5

Starting with a crude triphenyl phosphite with an acid value of 0.6, HAZEN coloring of 150 and a pungent smell, ten times the quantity of ammonia gas required to neutralize the residual acidity is added at 80°C. When the ammonium chloride has been filtered, the triphenyl phosphite has the following properties:

AV — 0.1
Coloring — 60 HAZEN
Odor — negligible

EXAMPLE 6

If the same procedure as in Example 4 is used but the ammonia gas is passed through at 20°C, triphenyl phosphite with the following properties is obtained after the product has been filtered and left to stand for 12 hours:

AV — 0.1
Coloring — 70 HAZEN
Odor — negligible

I claim:

1. A method of purifying crude triaryl phosphites having color, acid and odor, prepared by reacting phosphorous trichloride with an excess of a phenol, characterized in that the color, acid and odor are simultaneously reduced by treating the crude with a small quantity of at least one hydrogen compound of nitrogen, of a basic character selected from the group consisting of monoazotized (H NH$_2$) and diazotized (NH$_2$-NH$_2$) with the formation of a precipitate, and then separating the precipitate from the purified triaryl phosphites.

2. The method of claim 1 in which the hydrogen compound of nitrogen is ammonia introduced in an amount 2 to 10 times the amount required for neutralization of the acid.

3. The method of claim 1 in which the hydrogen compound of nitrogen is hydrazine hydrate.

4. The method of claim 2 in which the ammonia is introduced as a gas in the presence of an inert gas.

5. The method of claim 1 in which the triaryl phosphite is a triphenyl phosphite.

6. The method of claim 1 in which the triaryl phosphite is a trialkylphenyl phosphite.

7. The method of claim 1 in which the reaction temperature is from 20° to 120°C.

8. The method of claim 7 in which the reaction temperature is from 80° to 100°C.

9. The method of claim 1, in which the quantities of the hydrogen compound of nitrogen of a basic character are from 0.005 to 0.5% by weight relative to the phosphite.

10. The method as claimed in claim 1 in which the treatment is carried out in the presence of a solvent.

* * * * *